United States Patent [19]
Turner

[11] 3,958,883
[45] May 25, 1976

[54] RADIO FREQUENCY INDUCED PLASMA EXCITATION OF OPTICAL EMISSION SPECTROSCOPIC SAMPLES

[75] Inventor: Arthur S. Turner, Carlisle, Mass.

[73] Assignee: Baird-Atomic, Inc., Bedford, Mass.

[22] Filed: July 10, 1974

[21] Appl. No.: 487,168

[52] U.S. Cl. .............................. 356/85; 219/121 P; 315/111.5; 356/248; 356/79
[51] Int. Cl.² .......................................... G01J 3/30
[58] Field of Search .................. 356/80, 85, 86, 87, 356/79; 219/121 P; 315/111.5, 248, 344

[56] References Cited
UNITED STATES PATENTS

| | | | |
|---|---|---|---|
| 3,467,471 | 9/1969 | Greenfield et al. | 356/85 |
| 3,633,990 | 1/1972 | Baierlein | 356/80 |
| 3,846,024 | 11/1974 | Turner | 356/80 |

*Primary Examiner*—Vincent P. McGraw
*Attorney, Agent, or Firm*—Morse, Altman, Oates & Bello

[57] ABSTRACT

In a spectroscopic apparatus, a desolvated aerosol containing sample impurities to be analyzed is introduced into the center of a toroidal shaped plasma which is excited by an inductively coupled radio frequency power oscillator characterized by a single resonant circuit comprising an induction coil and its associated tuning capacitor, the plasma being produced by passing a gas stream along the axis of the induction coil. The single resonant circuit defined by the interconnection between the plate tank circuit and the grid tank circuit of the radio frequency power oscillator is such as to provide a common inductance for both circuits and to furnish power output and feedback for maintaining oscillation, whereby any detuning caused by introduction of the desolvated aerosol into the plasma does not affect the level of power transfer over a wide range.

12 Claims, 3 Drawing Figures

RADIO FREQUENCY INDUCED PLASMA EXCITATION OF OPTICAL EMISSION SPECTROSCOPIC SAMPLES

BACKGROUND OF THE INVENTION

1. Field of Invention

The present invention relates to plasma excitation of optical emission spectroscopy samples and, more particularly, is directed towards radio frequency power oscillators for plasma excitation of such samples.

2. Description of the Prior Art

Recent developments in high temperature technology have resulted in application of such technology to spectroscopic systems as typified in U.S. Pat. No. 3,467,471. In such systems, a plasma of annular form is produced by passing a gas stream along the axis of an induction coil of a radio frequency power source comprising frequency determiners such crystal resonators and LC circuits, the induction coil being part of a tuned LC circuits. A sample to be analyzed is introduced into the plasma, whereby the sample atoms are excited and radiate characteristics radiation which is detected and measured. Such systems have suffered from the disadvantages of limited practicality and utility in that the introduction of the sample into the plasma changes the impedance of the induction coil which results in a detuning of the circuit and a decrease in the power transferred to the plasma. The reduction in the power transferred to the plasma results in loss of the plasma or faulty analytical measurements. In order to overcome the problem of reduced power transfer due to detuning, the LC circuit is retuned manually. This retuning procedure is a time consuming operation which is generally unacceptable in a high volume production system.

SUMMARY OF THE INVENTION

It is an object of the present invention to provide a spectroscopic apparatus for radio frequency induced plasma excitation of optical emission spectroscopic samples which does not suffer from the heretoforementioned disadvantages. The present invention is characterized by an inductively coupled radio frequency excitation apparatus comprising a radio frequency power oscillator and associated power supply, a plasma torch and a nebulizer. The radio frequency power oscillator includes a vacuum tube and a single resonant circuit having an induction coil and its associated tuning capacitor. The induction coil encircles externally and coaxially a portion of the plasma torch, the encircled portion defining a plasma forming region. The nebulizer provides a desolvated aerosol containing sample impurities to be analyzed which is introduced into the center of a toroidal shaped plasma which is excited by the inductively couple radio frequency power oscillator. The plasma is produced by directing a gas stream along the axis of the induction coil. The single resonant circuit formed by interconnection of the plate tank circuit and grid tank circuit of the oscillator is characterized by a common inductance for both circuits. The single resonant circuit provides power output and feedback for maintaining oscillation so that any detuning caused by introduction of the desolvated aerosol does not affect the level of power transfer over a wide range. In consequence, the power transferred to the plasma is at a constant level and the excitation is maintained independently of the amount of sample introduced into the plasma. The combination of a spectroscopic apparatus and radio frequency excitation apparatus characterized by a radio frequency power oscillator having a single resonant circuit is such as to increase the practicality and utility of such RF induced plasma excitation apparatus.

Other and further objects of the present invention will in part be obvious and will in part appear hereinafter.

The invention accordingly comprises the machine possessing the construction, combination of elements, and arrangement of parts that are exemplified in the following detailed disclosure, the scope of which will be indicated in the appended claims.

BRIEF DESCRIPTION OF THE DRAWINGS

For a fuller understanding of the nature and objects of the present invention, reference should be had to the following detailed description taken in connection with the drawings wherein.

DETAILED DESCRIPTION OF THE INVENTION

Figure 1:
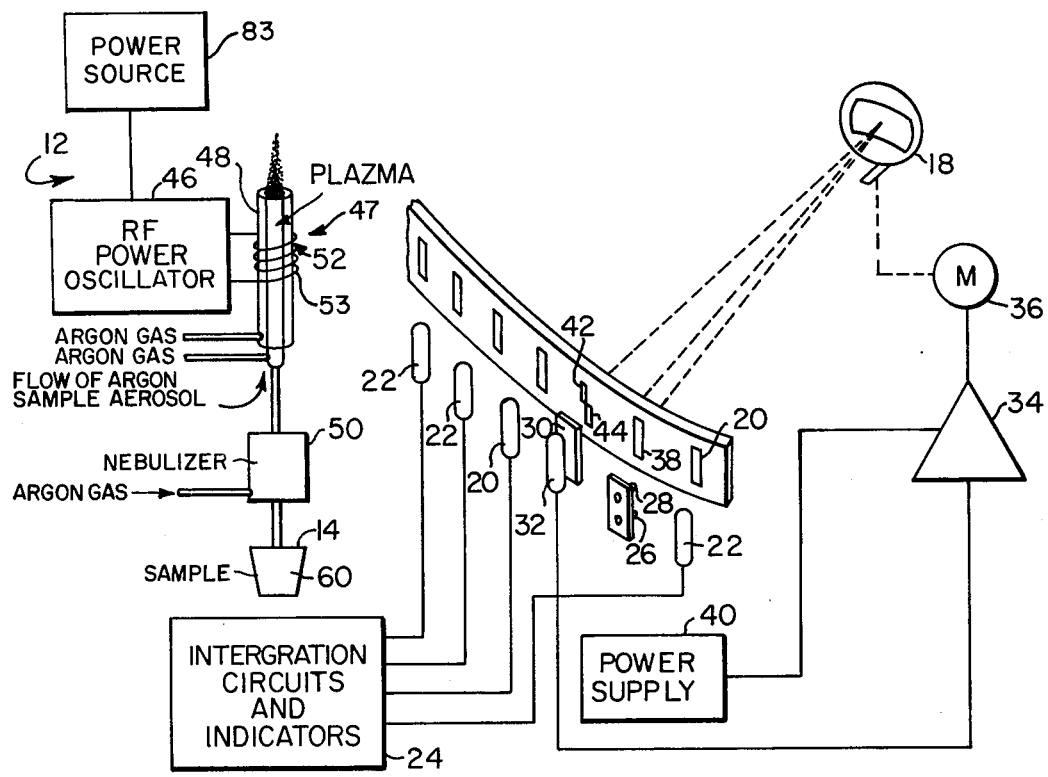
FIG. 1 is a perspective of a radio frequency induced plasma excited spectroscopic apparatus embodying the present invention.

Referring now to the drawings, particularly FIG. 1, there is shown a spectroscopic apparatus 10 which is characterized by a radio frequency excitation assembly 12 for radio frequency induced plasma excitation of optical emission spectroscopic samples. Spectroscopic apparatus 10 indicates the chemical composition of a specimen sample 14 by determining the intensity distribution of selected wavelengths of radiation emitted by specimen 14 when excited by radio frequency excitation assembly 12. The radiation emitted by excited specimen 14 is directed through an entrance slit 16 towards a concave diffraction grating 18 in order to produce a spectrum. Preselected lines of the spectrum are imaged on exit slits 20 and detected by photodetectors 22. The intensities of these spectrum lines are indicated by means of photodetectors 28 in association with appropriate integrating circuits and indicators 24.

In order to minimize even slight disturbances of the spatial relationships among the various aforementioned components, they are mounted on a sturdy A-shaped frame of the type shown in U.S. Pat. No. 3,056,330 which issued from patent application Ser. No. 9,618 filed on the 18th of February 1960 in the name of Jason L. Saunderson for Spectroscopic Apparatus and assigned to the assignee of this application. Proper orientation of diffraction grating 18 with respect to entrance slit 16 and exit slits 20 is maintained by means of an automatic servo system now to be described.

The servo system comprises a pair of solid state light sources 26, and 28, a filter 30, a photo detector 32, a servo amplifier 34, and a servo motor 36. This servo system is photoelectrically controlled by two beams of light emitted by sources 26 and 28 which are energized sequentially on alternate half cycles of power line voltage. These beams are directed through a vertical entrance slit 38 towards diffraction grating 18, the intensity of each beam being controlled by a power supply 40. Grating 18 directs these beams back towards slightly offset upper and lower exit slits 42 and 44 for detection by photo detector 32 via filter 30. Normally, the servo system is adjusted so that when diffraction grating 18 is properly oriented, the upper and lower beams as shown in dotted lines are transmitted in equal intensity through slits 42 and 44, respectively. In the illustrated embodiment, filter 30 is a long wavelength pass filter, for example a sharp cut-on red glass filter such as that sold by Corning under the trade designation Type 3-67. When diffraction grating 18 becomes improperly oriented, more of one of the beams and less of the other are transmitted through their correlative exit slits. For example, a slight disorientation of diffraction grating 18 might cause the upper and lower beams to move to the left, as viewed in the drawings, so that the intensity of the beam transmitted through upper slit 42 would be greater than the intensity of the beam transmitted through lower slit 44. The resulting unbalance in the upper and lower beam intensities is summed in photo detector 32 which generates an error signal related to the unbalance. This error signal is applied to servo amplifier 34 which generates a drive signal for controlling servo motor 36. The servo motor is driven in a direction which reorients diffraction grating 18 so that the upper and lower beams are transmitted in equal intensity through exit slits 42 and 44, respectively. In the illustrated embodiment, light sources 26, 28 with entrance slit 38 and offset exit slits 42, 44 with photo-detector 32 are positioned symmetrically about the normal of diffraction grating 18. Vertical entrance slit 38 is positioned at a selected point on the focal curve such that the light emitted by light sources 26, 28 is diffracted at angles falling outside the spectral range utilized by spectroscopic apparatus 10. As previously noted, spectroscopic apparatus 10 indicates the chemical composition of specimen sample 14, which is specified by the intensity distribution of characteristic wavelengths emitted by sample 14 when excited by radio frequency excitation assembly 12.

Figure 2:
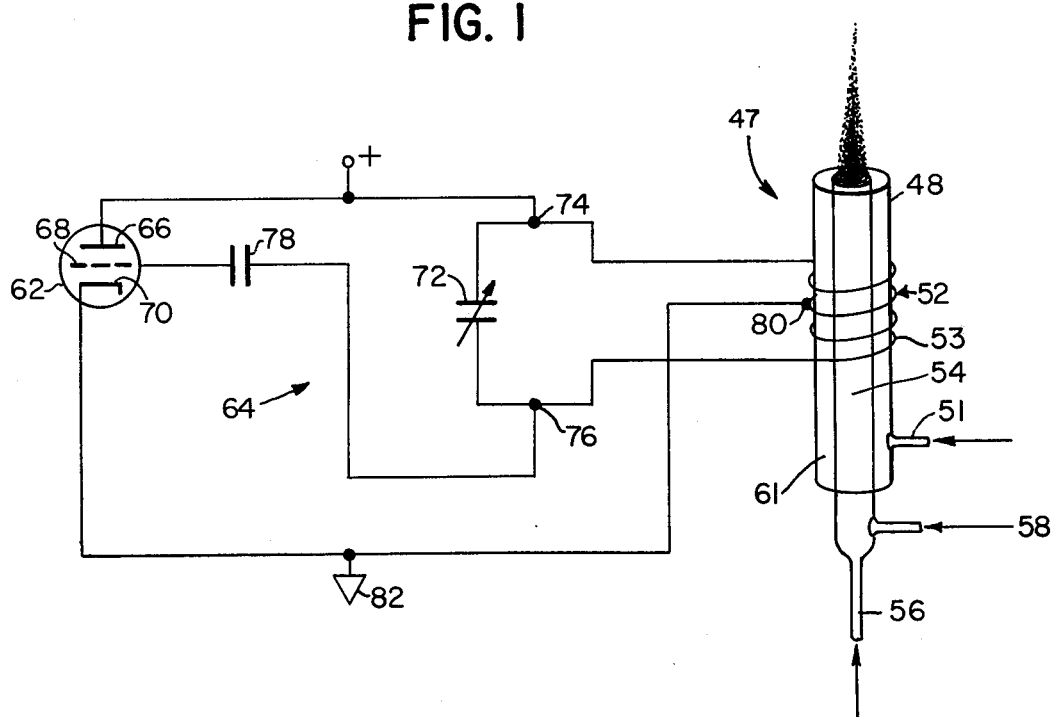
FIG. 2 is a simplified schematic diagram of the radio frequency power oscillator of FIG. 1.

As shown in FIGS. 1 and 2, radio frequency excitation apparatus 12 comprises a radio frequency (RF) power oscillator 46 and an associated power supply 83, a plasma torch 47, and a nebulizer 50. As viewed in the drawings, plasma torch 47 includes an outer tubular vessel 48 which is opened at its upper end and closed at its bottom end. At the closed end of vessel 48 there is provided a tangential inlet port 51 for an insulating gas such as argon. RF power oscillator 46 includes an induction coil 52 which encircles externally and coaxially a portion of outer vessel 48, the encircled portion defining a plasma forming region. In the illustrated embodiment, by way of example, induction coil 52 provides an inductance of 0.3 $\mu$h and comprises three turns of copper tubing 53 having a length of approximately 50.8 mm and an internal diameter of approximately 24 mm. An inner tubular vessel 54 is mounted coaxially within outer tubular vessel 48, the upper end of inner vessel 54 being opened and in registration with the opened end of outer vessel 48, the lower end of inner vessel 54 projecting outwardly from the closed end of outer vessel 48. The projecting portion of inner vessel 54 converges and forms a coaxial inlet port 56 for a desolvated aerosol containing sample impurities from nebulizer 50. Inner vessel 54 is provided with a tangential inlet port 58 for a plasma forming gas such as argon, inlet port 58 being interposed between the closed end of outer vessel 48 and the narrowed portion of inner vessel 54. The desolvated aerosol is produced by nebulizer 50 which receives sample 14 within a container 60. Inlet port 56 receives a dry inert gas supported aerosol containing the sample impurities which are to be analyzed by aspirating the sample solution with the inert gas, for example argon, and desolvating the resulting aerosol. Desolvation is accomplished in nebulizer 50 by means of mechanical baffling, thermal heating and condensers. The desolvated aerosol containing sample impurities is introduced into the center of a toroidal shaped plasma within inner vessel 54, the plasma being excited by inductively coupled radio frequency power oscillator 46. It is to be noted that the insulating gas, for example argon, which is introduced through inlet port 50 into a cylindrical chamber 61 formed between outer vessel 48 and inner vessel 54 operates as a shield for the excited plasma. As hereinafter described, in the preferred embodiment, the relationship between the exciting frequency and the plasma diameter is such that the skin effect creates a toroidal or doughnut-shaped cross-sectional plasma. The desolvated aerosol is directed into the center of the plasma for greater excitation and sensitivity than that which is obtainable with a uniform plasma.

Radio frequency power oscillator 46 comprises a vacuum tube 62 and a single resonant circuit 64. Vacuum tube 62 includes a plate 66, a grid 68, and a cathode 70. Resonant circuit 64 includes induction coil 52 and an associated tuning capacitor 72. One side of capacitor 72 and one side of coil 52 are connected at a junction 74 which is futher connected to plate 66. The other side of capacitor 72 and the other side of coil 52 are connected at a junction 76 which is further connected to grid 68 via a capacitor 78 provided for DC isolation. A tap 80 of coil 52 and cathode 70 are connected to a return 82, for example, ground. From the foregoing description, it will be appreciated that the plate tank circuit and the grid tank circuit are connected in such a manner that common inductance is provided for both circuits. That is, the circuit interconnections of radio frequency power oscillator 46 are such that a continuously tuned circuit is provided between the plate tank circuit and the grid tank circuit. In consequence, the power output furnished by radio frequency power oscillator 46 is constant regardless of impedance changes caused by introduction of the desolvated aerosol into the plasma. Induction coil 52 and its associated tuning capacitor 72 serve to provide power output and feedback to maintain oscillation, whereby detuning caused by introduction of the desolvated aerosol does not affect the level of power transfer over rather wide limits. In the illustrated embodiment, radio frequency power oscillator 46 is operated at a basic frequency of 30 MHz and is variable in the range of 10 MHz to 60 MHz. A detailed schematic diagram of radio frequency power oscillator 46 and associated power supply 83 is presented in FIG. 3.

Figure 3:
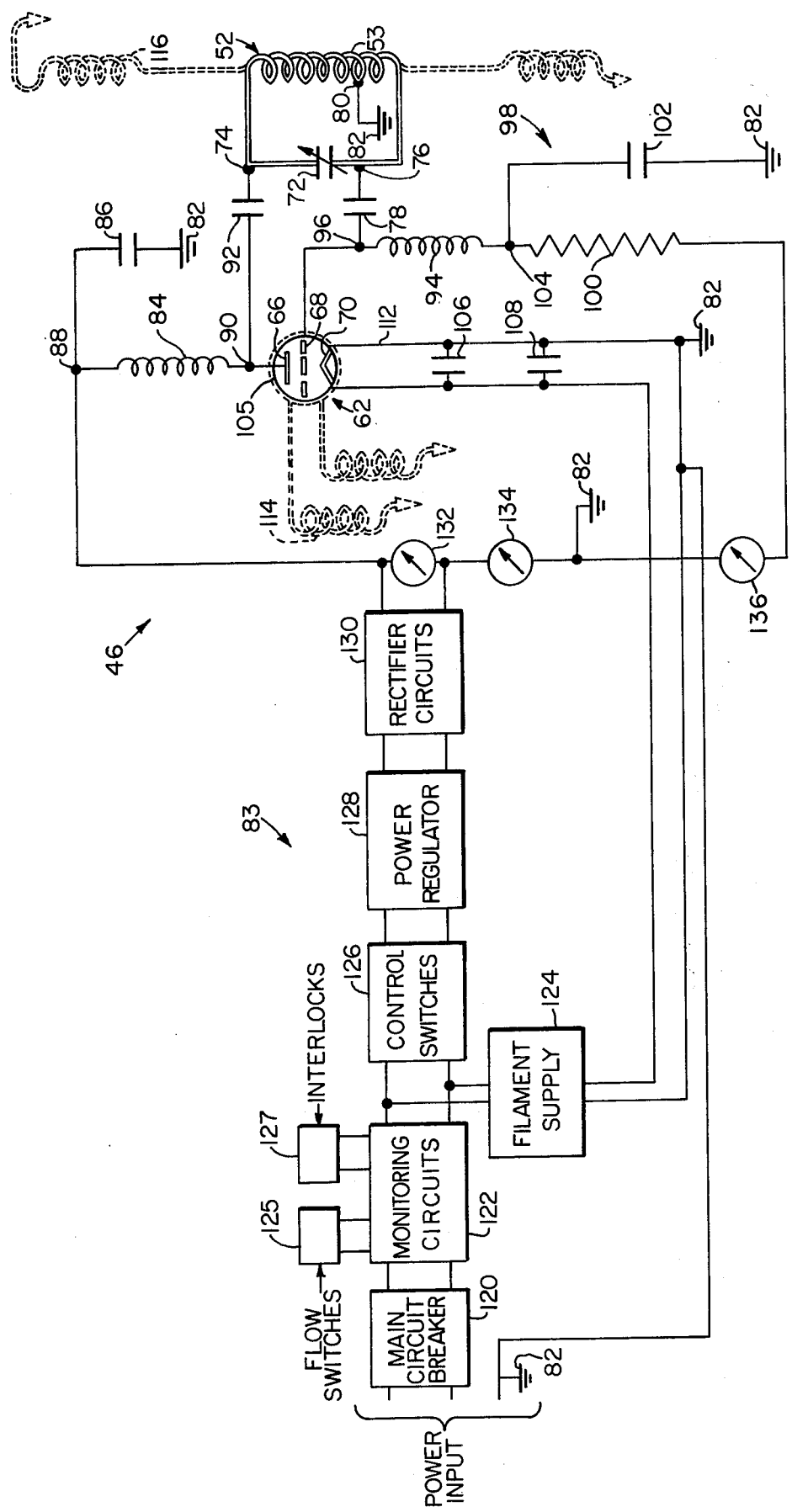
FIG. 3 is a detailed schematic diagram of the radio frequency power oscillator of FIG. 2.

Referring now to FIG. 3, there is shown radio frequency power oscillator 46 and associated power supply 83. A plate voltage generated by power supply 83 is applied to plate 66 of vacuum tube 62 through a plate RF choke and low pass filter circuit comprising an inductor 84 and a capacitor 86. One side of plate RF choke 84 and one side of capacitor 86 are joined at a junction 88, the other side of RF choke 84 is connected to a junction 90 and the other side of capacitor 86 is coupled to return 82. A capacitor 92, for DC isolation, is connected between junctions 90 and 74, junction 90 being futher connected to plate 66. One side of a grid RF choke 94 is connected to a junction 96 of grid 68 and capacitor 78. The other side of grid RF choke 94 is connected to a low pass filter 98 which includes a resistor 100 and a capacitor 102; grid RF choke 94, resistor 100 and capacitor 102 being joined at a junction 104. The free side of capacitor 102 is coupled to return 82 and the free side of resistor 100 is connected to power supply 83. Capacitors 106, 108, in parallel, are connected between cathode leads 110, 112. In the illustrated embodiment, vacuum tube 62 is provided with a cooling jacket 105 and is cooled by means of a liquid coolant which is flowing through a coolant line 114 and induction coil 52 is cooled by passing a coolant which is flowing in a coolant line 116 through copper tubing 53. Additional cooling may be provided by means of a fan. As previously noted, the voltages applied to radio frequency power oscillator 46 are generated by power supply 83.

Power supply 83 includes a main circuit breaker 120 through which power from an external source (not shown) is applied. The voltage at the output side of breaker 120 is coupled through monitoring circuits 122 to a filament supply 124 and control switches 126. Monitoring circuits 122 prevent application of filament voltage when flow switches 125 associated with coolant lines 114, 116 are opened, an indication of insufficient coolant flow, and also prevent application of plate voltage if either interlock switches 127 or flow switches 125 are opened. Filament power supply 124 is connected to leads 110 and 112. Control switches 126 feed a power regulator 128 which is further connected to rectifier circuits 130. Plate voltage as at the output of rectifier circuits 130, the level of which is controlled by regulator 128, is applied to junction 88 of radio frequency power source 46. In the preferred embodiment, power supply 83 includes a plate voltmeter 132 and a plate ammeter 134 at the output of rectifier circuits 130 for monitoring plate voltage and plate current, respectively. Power supply 83 includes also a grid ammeter 136 connected to resistor 100 for monitoring grid current.

From the foregoing description, it will be appreciated that the present invention provides a spectroscopic apparatus and a radio frequency excitation apparatus comprising a radio frequency power oscillator characterized by a single resonant circuit including an induction coil and its associated tuning capacitor for providing output power and feedback to maintain oscillation, whereby detuning caused by introduction of the desolvated aerosol containing the sample to be analyzed into the plasma does not affect the level of power transfer over rather wide limits. That is, the plate tank circuit and the grid tank circuit are interconnected so that there is a common inductance for both circuits and the power output is constant regardless of impedance changes caused by introduction of the desolvated aerosol into the plasma. This invention greatly increases the practicality and utility of the RF induced plasma for commercial application.

Since certain changes may be made in the foregoing disclosure without departing from the scope of the invention herein involved, it is intended that all matter contained in the above description and depicted in the accompanying drawings be construed in an illustrative and not in a limiting sense.

What is claimed is:

1. A radio frequency excitation apparatus for exciting a spectroscopic sample, said excited spectroscopic sample emitting characteristic radiation, said apparatus comprising:

a. radio frequency power oscillator means having a plate tank circuit and a grid tank circuit defining a single resonant circuit including an induction coil and a tuning capacitor, said induction coil in parallel with said turning capacitor, said plate tank circuit and said grid tank circuit having a common inductance;

b. plasma torch means, said induction coil externally and coaxially encircling a portion of said plasma torch means, said encircled portion of said plasma torch means defining a plasma forming region, said radio frequency power oscillator means exciting a plasma forming gas within said plasma forming region; and c. means for introducing the spectoroscopic sample into said excited plasma, the spectroscopic sample introduced into said excited plasma emitting characteristic radiation.

2. A radio frequency excitation apparatus for exciting a spectroscopic sample, said excited spectroscopic sample emitting characteristic radiation, said apparatus comprising:

a. radio frequency power oscillator means having a plate tank circuit and a grid tank circuit defining a single resonant circuit including an induction coil and a tuning capacitor, said induction coil in parallel with said tuning capacitor, said plate tank circuit and said grid tank circuit having a common inductance;

b. plasma torch means, said induction coil externally and coaxially encircling a portion of said plasma torch means, said encircled portion of said plasma torch means defining a plasma forming region, said radio frequency power oscillator means exciting a plasma forming gas within said plasma forming region;

c. means for introducing the spectroscopic sample into said excited plasma, the spectroscopic sample introduced into said excited plasma emitting characteristic radiation; and d. power supply means operativley connected to said radio frequency power oscillator means.

3. A radio frequency excitation apparatus for exciting a spectroscopic sample, said excited spectroscopic sample emitting characteristic radiation, said apparatus comprising:

a. radio frequency power oscillator means having a plate tank circuit and a grid tank circuit defining a single resonant circuit including an induction coil and a tuning capacitor, said plate tank circuit and said grid tank circuit having a common inductance, said radio frequency power oscillator means including a dc isolation capacitor and vacuum tube means having a plate, a grid, and a cathode, said induction coil in parallel with said tuning capacitor, one side of said induction coil and said tuning capacitor operatively connected to said plate, the other side of said induction coil and said tuning capacitor operatively connected to said grid via said dc isolation capacitor, and induction coil having a tap, said cathode and said tap operatively connected to a return, said induction coil being common to said plate tank circuit and said grid tank circuit;

b. plasma torch means, said induction coil externally and coaxially encircling a portion of said plasma torch means, said encircled portion of said plasma torch means defining a plasma forming region, said radio frequency power oscillator means exciting a plasma forming gas within said plasma forming region; and c. means for introducing the spectroscopic sample into said excited plasma, the spectroscopic sample introduced into said excited plasma emitting characteristic radiation.

4. A radio frequency excitation apparatus for exciting a spectroscopic sample, said excited spectroscopic sample emitting characteristic radiation, said apparatus comprising:

a. radio frequency power oscillator means having a plate tank circuit and a grid tank circuit defining single resonant circuit including an induction coil and a tuning capacitor, said plate tank circuit and said grid tank circuit having a common inductance, said radio frequency power oscillator means including a capacitor for dc isolation and vacuum tube means having a plate, a grid, and a cathode, said induction coil in parallel with said tuning capacitor, one side of said tuning capacitor operatively connected to said plate, the other side of said induction coil and the other side of said tuning capacitor operatively connected to said grid via said dc isolation capacitor, said induction coil having a tap operatively connected to a return, said induction coil being common to said plate tank circuit and said grid tank circuit;

b. plasma torch means, said induction coil externally and coaxially encircling a portion of said plasma torch means, said encircled portion of said plasma torch means defining a plasma forming region, said radio frequency power oscillator means exciting a plasma forming gas within said plasma forming region;

c. means for introducing the spectroscopic sample into said excited plasma, the spectroscopic sample introduced into said excited plasma emitting characteristic radiation; and d. power supply means operatively connected to said radio frequency power oscillator means.

5. The radio frequency excitation apparatus as claimed in claim 4 wherein said plasma torch means includes:

a. an outer tubular vessel opened at one end and closed at an opposite end, a tangential inlet port for an insulating gas formed near the closed end of said outer tubular vessel; and b. an inner tubular vessel coaxial mounted within said outer tubular vessel, a chamber for said insulating gas formed between said outer tubular vessel and said inner tubular vessel, said inner tubular vessel opened at one end, the opened end of said inner tubular vessel in registration with the opened end of said outer tubular vessel, said inner tubular vessel projecting from said closed end of said outer tubular vessel, said projecting portion of said inner tubular vessel having a narrowed portion defining a coaxial inlet port for introduction of the spectroscopic sample, a tangential inlet port for a plasma forming gas formed in said projecting portion of said inner tubular vessel.

6. The radio frequency excitation apparatus as claimed in claim 5 wherein said means for introducing the spectroscopic sample includes nebulizer means for providing a desolvated aerosol containing the spectroscopic sample, said desolvated aerosol introduced into said coaxial inlet port formed in said inner tubular vessel.

7. A radio frequency excitation apparatus for exciting a spectroscopic sample, said excited spectroscopic sample emitting characteristic radiation, said apparatus comprising:

a. radio frequency power oscillator means having a plate tank circuit and a grid tank circuit defining a single resonant circuit including an induction coil and a tuning capacitor, said plate tank circuit and said grid tank circuit having a common inductance, said radio frequency power oscillator means including vacuum tube means having a plate, a grid, and a cathode, first and second capacitors for dc isolation, a plate RF choke, and a grid RF choke, said plate RF choke connected to said plate and one side of said first capacitor, the other side of said first capacitor connected to one side of said tuning capacitor and one side of said induction coil, said tuning capacitor and said induction coil in parallel, the other sides of said tuning capacitor and said induction coil connected to one side of said second capacitor, the other side of said second capacitor connected to said grid and said grid Rf choke, said induction coil having a tap which is connected to ground;

b. plasma torch means, said induction coil externally and coaxially encircling a portion of said plasma torch means, said encircled portion of said plasma torch means defining a plasma forming region, said radio frequency power oscillator means exciting a plasma forming gas within said plasma region;

c. means for introducing the spectroscopic sample into said excited plasma, the spectroscopic sample introduced into said excited plasma emitting characteristic radiation; and d. power supply means operatively connected to said radio frequency power oscillator means.

8. The radio frequency excitation apparatus as claimed in claim 7 wherein said power supply means includes:

a. circuit breaker means through which input power is applied;

b. filament supply means operatively connected to said circuit breaker means and said vacuum tube means, said filament supply means generating filament voltage for said vacuum tube means;

c. power regulator means operatively connected to said circuit breaker means; and d. rectifier means operatively connected to said power regulator means and said vacuum tube means, said rectifier means generating plate voltage for said vacuum tube means, said power regulator means controlling the level of said plate voltage.

9. A spectroscopic apparatus comprising:

a. a radio frequency excitation apparatus for exciting a spectroscopic sample, said excited spectroscopic sample emitting characteristic radiation, said radio frequency excitation apparatus including a radio frequency power oscillator and an associated power supply, a plasma torch, and injection means, said radio frequency power oscillator comprising a single resonant circuit which includes an induction coil and a tuning capacitor, said induction coil in parallel with said tuning capacitor, a plate tank circuit and a grid tank circuit of said radio frequency power oscillator having a common inductance, said induction coil externally and coaxially encircling a portion of said plasma torch, said encircled portion of said plasma torch defining a plasma forming region, said radio frequency power oscillator exciting a plasma forming gas within said plasma forming region, said injection means introducing said spectroscopic sample into said excited plasma, said introduced spectroscopic sample being excited and emitting characteristic radaition;

b. entrance slit means through which said characteristic radiation is directed;

c. grating means for diffracting said characteristic radiation from said entrance slit means into a distribution of spectrum lines;

d. a plurality of exit slit means on which said spectrum lines are imaged; and e. means for detecting and processing said spectrum lines imaged on said exit slit means for indicating the chemical composition of said spectroscopic sample; and f. servo means operatively connected to said grating means for alignment of said grating means with respect to said entrance slit means and said exit slit means.

10. A spectroscopic apparatus comprising:

a. a radio frequency excitation apparatus for exciting a spectroscopic sample, said excited spectroscopic sample emitting characteristic radiation, said radio frequency excitation apparatus including a radio frequency power oscillator and an associated power supply, a plasma torch, and injection means, said radio frequency power oscillator comprising a single resonant circuit which includes an induction coil and a tuning capacitor, a plate circuit and a grid tank circuit of said radio frequency power oscillator having a common inductance, said radio frequency power oscillator including a capacitor for dc isolation and vacuum tube means having a plate, a grid, and a cathode, said induction coil in parallel with said tuning capacitor, one side of said tuning capacitor operatively connected to said plate, the other side of said induction coil and the other side of said tuning capacitor operatively connected to said grid via said dc isolation capacitor, said induction coil having a tap operatively connected to a return, said induction coil being common to said plate tank circuit and said grid tank circuit, said induction coil externally and coaxially encircling a portion of said plasma torch, said encircled portion of said plasma torch defining a plasma forming region, said radio frequency power oscillator exciting a plasma forming gas within said plasma forming region, said injection means introducing said spectroscopic sample into said excited plasma, said introduced stpectroscopic sample being excited and emitting characteristic radiation;

b. entrance slit means through which said characteristic radiation is directed;

c. grating means for diffracting said characteristic radiation from said entrance slit means into a distribution of spectrum lines;

d. a plurality of exit slit means on which said spectrum lines are imaged;

e. means for detecting and processing said spectrum lines imaged on said exit composition of said spectroscopic sample; and f. servo means operatively connected to said grating means for alignment of said grating means with respect ot said entrance slit means and said exit slit means.

11. The radio frequency excitation apparatus as claimed in claim 10 wherein said plasma torch means includes:

a. an outer tubular vessel opened at one end and closed at an opposite end, a tangential inlet port for an insulating gas formed near the closed end of said outer tubular vessel; and b. an inner tubular vessel coaxial mounted within said outer tubular vessel, a chamber for said insulating gas formed between said outer tubular vessel and said inner tubular vessel, said inner tubular vessel opened at one end, said inner tubular vessel projecting from said closed end of said outer tubular vessel, said projecting portion of said inner tubular vessel having a narrowed portion defining a coaxial inlet port for introduction of the spectroscopic sample, a tangential inlet port for a plasma forming gas formed in said projecting portion of said inner tubular vessel.

12. The radio frequency excitation apparatus as claimed in claim 11 wherein said injection means includes means for providing a desolvated aerosol containing the spectroscopic sample, said desolvated aerosol introduced into said coaxial inlet port formed in said inner tubular vessel.

* * * * *